United States Patent
Sasaki et al.

(10) Patent No.: US 10,548,558 B2
(45) Date of Patent: Feb. 4, 2020

(54) CONTROL APPARATUS FOR RADIOGRAPHIC SYSTEM

(71) Applicant: CANON KABUSHIKI KAISHA, Tokyo (JP)

(72) Inventors: Hiroshi Sasaki, Kawasaki (JP); Tadahiko Iijima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 258 days.

(21) Appl. No.: 15/827,474

(22) Filed: Nov. 30, 2017

(65) Prior Publication Data

US 2018/0153496 A1    Jun. 7, 2018

(30) Foreign Application Priority Data

Dec. 7, 2016 (JP) .................................. 2016-237690

(51) Int. Cl.
    *G01T 1/17*    (2006.01)
    *A61B 6/00*    (2006.01)
(52) U.S. Cl.
    CPC .................. *A61B 6/54* (2013.01); *A61B 6/40* (2013.01); *A61B 6/56* (2013.01)

(58) Field of Classification Search
    CPC .... A61B 6/54; G01T 1/17; G01T 1/02; G01N 23/04
    See application file for complete search history.

(56) References Cited

U.S. PATENT DOCUMENTS

2015/0378030 A1\* 12/2015 Tamura .................. G01N 23/04
                                                       378/98.2

FOREIGN PATENT DOCUMENTS

JP        2012-045159 A     3/2012
JP        2016-140513 A     8/2016

\* cited by examiner

*Primary Examiner* — Don K Wong
(74) *Attorney, Agent, or Firm* — Canon U.S.A., Inc. IP Division (57) ABSTRACT

In a radiographic system in which long length imaging is performed by combining a plurality of radiographic apparatuses whose preparatory periods from a request of radiation exposure to start of accumulation are different, a control apparatus controls the plurality of radiographic apparatuses and a radiation generation apparatus so that an exposure period of the radiation generation apparatus is included in a period in which accumulation periods of all the radiographic apparatuses overlap.

20 Claims, 9 Drawing Sheets

CONTROL APPARATUS FOR RADIOGRAPHIC SYSTEM

BACKGROUND

Field

The present disclosure relates to a radiographic system in which long length imaging is performed by using a plurality of radiographic apparatuses and a control apparatus.

Description of the Related Art

In recent years, there has been a demand in the medical field for imaging of a long observation area (hereinafter, referred to as long length imaging), by which imaging of an entire spiral cord, an entire lower limb, or an entire body can be performed in order to discover a distortion or abnormality of a body of a subject. Japanese Patent Laid-Open No. 2012-045159 discloses a radiographic image capture system in which a plurality of electronic cassettes are placed adjacent to each other in a predetermined direction. It is also disclosed that each of the electronic cassettes independently performs a transition operation from a state of performing a preparatory operation to a state of performing an imaging operation in response to a transition command. Japanese Patent Laid-Open No. 2016-140513 discloses a control apparatus for long length imaging that receives, from each of a plurality of radiographic units, state information indicating whether each of the plurality of radiographic units is in a state prepared for acquisition of a radiographic image.

In conventional long length imaging, when an exposure period of X-rays does not fall within accumulation periods of signals in imaging operations of all portable radiographic apparatuses, an artifact can appear in a captured image. In particular, when imaging apparatuses that are different in a preparatory period from start of a preparatory operation to start of an imaging operation are used, in an imaging apparatus whose preparatory period is shorter than the exposure period of X-rays, the exposure of X-rays may not be completed when the accumulation ends and the exposure of X-rays can be continued even after the end of the accumulation. Thus, in a case where a long length imaging system in which imaging apparatuses whose preparatory periods are different are combined is used, it is difficult to control the imaging apparatuses compared to a case where the same imaging apparatus is used.

SUMMARY OF THE INVENTION

In view of the above, the present disclosure provides a radiographic system that obtains an improved long length image even when imaging apparatuses whose preparatory periods are different are used.

The present disclosure provides a control apparatus for a radiographic system in which long length imaging is performed using a plurality of radiographic apparatuses that each includes an accumulation period enabling accumulation of electric charge corresponding to incident radiation and a preparatory period including a period to perform initialization operation, and at least one of the plurality of radiographic apparatuses includes a different preparatory period that includes a memory storing instructions and a control circuit that executes the instructions to control the plurality of radiographic apparatuses and a radiation generation apparatus so that an exposure period of the radiation generation apparatus is included in a period in which accumulation periods of all the plurality of radiographic apparatuses overlap.

Further, features of the present disclosure will become apparent from the following description of exemplary embodiments with reference to the attached drawings.

DESCRIPTION OF THE EMBODIMENTS

Hereinafter, embodiments will be described with reference to drawings.

Figure 1:
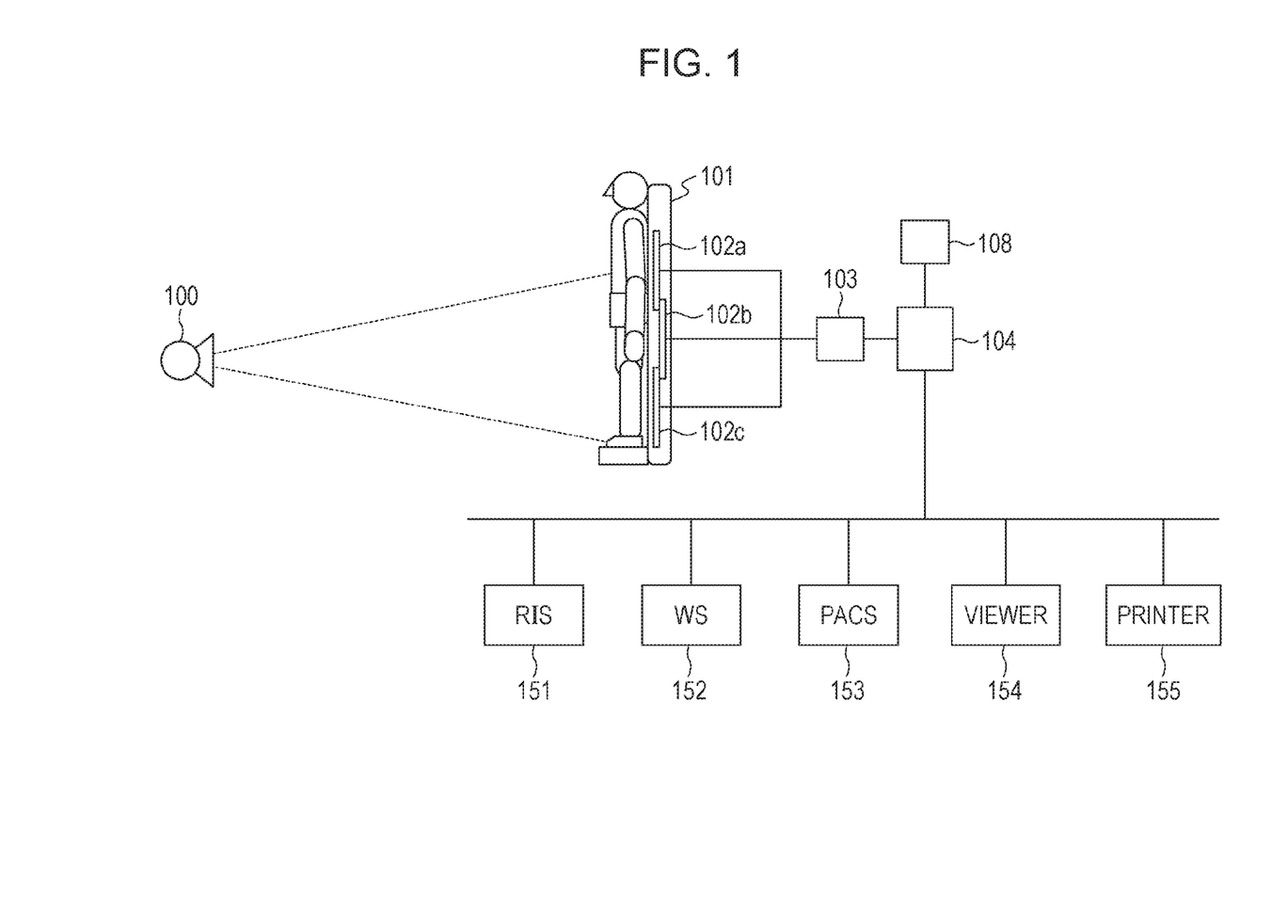
FIG. 1 is a conceptual view illustrating a configuration of a radiographic system.

FIG. 1 illustrates a configuration of an information system including a radiographic system according to the present embodiment. A long length imaging system using X-rays is illustrated as the radiographic system. An RIS (Radiology Information System) 151 manages radiography orders and transmits the radiography orders to the radiographic system. A WS (Work Station) 152 is an image processing terminal, and processes a captured radiographic image and acquires an image for diagnosis. A PACS (Picture Archiving and Communication System) 153 is a database system in which medical images captured by the radiographic system or another modality are stored. A viewer 154 is a terminal for diagnostic imaging and reads out an image stored in the PACS 153 or the like to display the image on a display. A printer 155 is, for example, a film printer, and outputs the image stored in the PACS 153 on a film.

In the long length imaging system, a radiation generation apparatus 100 emits radiation simultaneously to a plurality of cassettes 102a (cassetteA), 102b (cassetteB), and 102c (cassetteC). Radiographic images captured by the cassettes (radiographic apparatuses) 102 through the emission of the radiation are transmitted to a control apparatus 104 for the radiographic system.

The control apparatus 104 is a PC (personal computer) and performs control of the radiation generation apparatus 100 and the plurality of cassettes 102. The control apparatus 104 generates a long length image by performing image processing, including image stitching processing, for a plurality of radiographic images acquired by the cassettes 102 and causes the long length image to be displayed on a touch panel monitor 108. The control apparatus 104 generates a DICOM (Digital Imaging and Communications in Medicine) image based on the long length image and additional information, such as an imaging condition of the long length image, and transmits the DICOM image to the WS 152 or the PACS 153.

The imaging order for the long length imaging is transmitted from the RIS 151 to the control apparatus 104. The control apparatus 104 receives, from the RIS 151, an imaging information ID indicating the long length imaging and information about an imaging site, such as an entire lower limb or an entire spine, which needs to be subjected to the long length imaging. The control apparatus 104 then reads out an imaging condition corresponding to the received information from a storage unit.

The cassettes 102 are arranged in such a manner that a region imaged by the cassetteA 102a and a region imaged by the cassetteB 102b partially overlap each other to achieve a continuous imaging region. Thereby, a structure (end of the cassetteA 102a) appears in the radiographic image acquired by the cassetteB 102b. On a platform 101, only a cassette arranged in the middle from among the cassettes arranged in the order is located at a position farther away from the radiation generation apparatus 100 than the other cassettes, and is arranged in such a manner that an imaging region partially overlaps the imaging regions of the other cassettes. Such an arrangement enables reducing a region in which the structure appears. The radiographic image in which the structure appears is subjected to image processing using correction data for correcting the structure so that the appearance of the structure is reduced.

Figure 2:
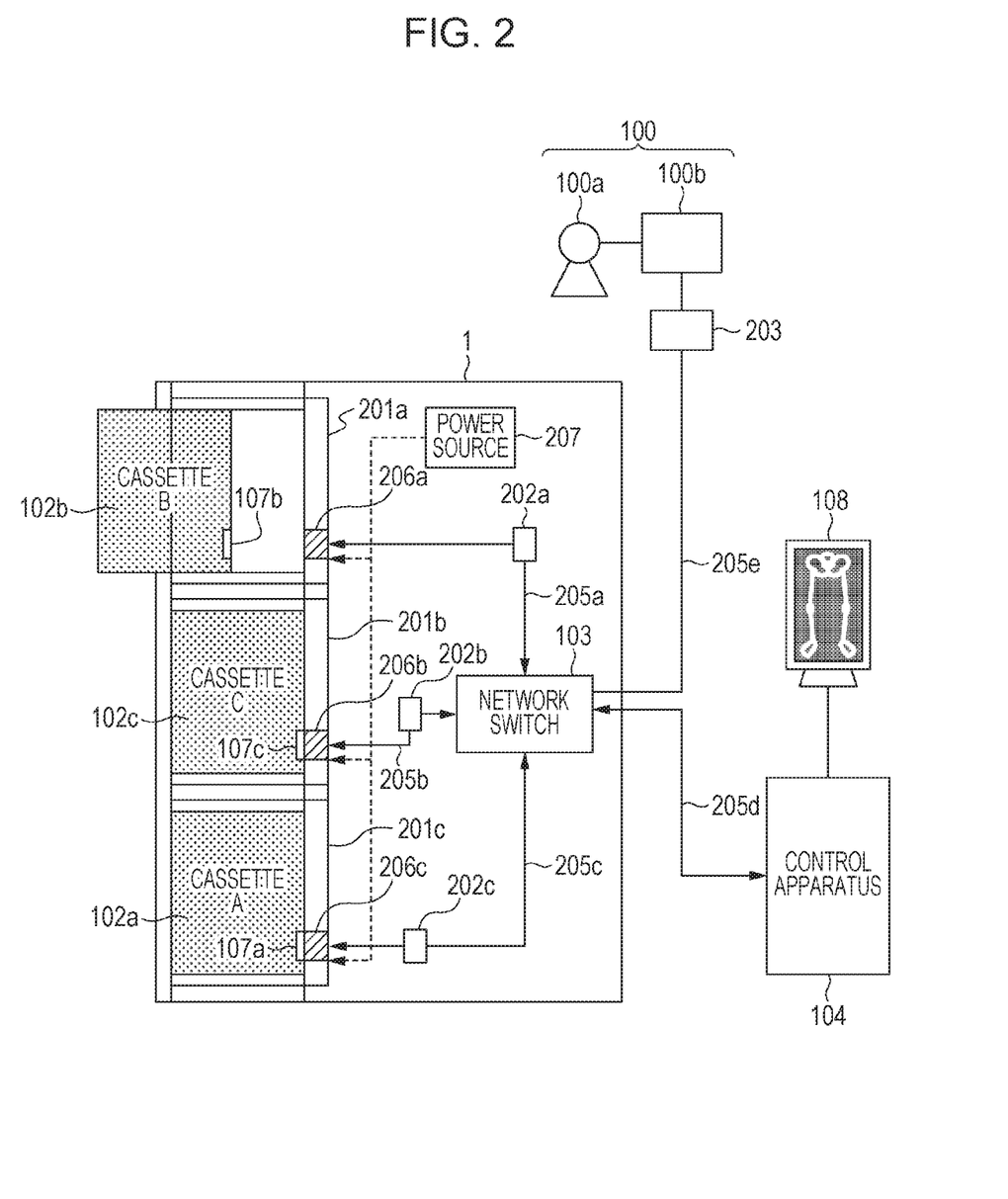
FIG. 2 is a schematic view illustrating a configuration of a long length imaging system.

A configuration of the long length imaging system according to the present embodiment will be described in detail with reference to FIG. 2. The radiation generation apparatus 100 includes a radiation source 100a and a generation control unit 100b that controls the radiation source 100a. The radiation source 100a is constituted by a diaphragm for setting a range to be irradiated with the radiation and a radiation source for generating the radiation. An irradiation switch is connected to the generation control unit 100b to input a signal for instructing timing of starting the irradiation to the generation control unit 100b. The radiation generation apparatus 100 can also include an interface unit 203 that communicates with the cassettes 102. In this case, the radiation generation apparatus 100 and the platform 101 are communicably connected via a network cable 205e, such as Ethernet. The control apparatus 104 is communicably connected to the platform 101 via a network cable 205d.

The platform 101 includes, as holding units for fixing the plurality of cassettes 102, housing units 201 in which the cassettes 102 are housed at three fixing positions. The positions of platform connectors 206 and imaging unit connectors 107 that are provided alongside walls of the housing units 201 are determined so that the respective connectors are fitted to each other when the cassettes 102 are fixed in the housing units 201.

The platform connectors 206 are connected to a relay 103 via network cables 205. The platform connectors 206 are also connected to the imaging unit connectors 107 of the cassettes 102. In the present embodiment, an imaging unit connector 107b of the cassette 102b is connected to a platform connector 206a, an imaging unit connector 107c of the cassette 102c is connected to a platform connector 206b, and an imaging unit connector 107a of the cassette 102a is connected to a platform connector 206c.

The relay 103 is a network switch and one of a plurality of physical ports is extended out of the platform 101 to be connectable to the control apparatus 104. The port is wired in a fixed manner to be connected to a communication port of the control apparatus 104 when the platform 101 and the control apparatus 104 are installed in a use environment of a user. The remaining ports are wired to be connected to the platform connectors 206 at the fixation positions of the cassettes. Such wiring is fixed when the platform 101 is manufactured so that corresponding relationships between the platform connectors 206 and the physical ports of the relay 103 do not change during usage by the user.

The platform 101 can also include a power source 207 that supplies power to the cassettes 102. In this case, two cable systems of a network cable and a power source cable are connected to each of the platform connectors 206. Instead of the power source 207, power source units 202a, 202b, and 202c can be provided with respect to housing units 201a, 201b, and 201c, respectively. In this case, two cable systems of a communication cable and a power source cable are provided between the platform connectors 206 and the power source units 202 and connection of a communication cable is provided between the power source units 202 and the relay 103.

Radiographic image data captured by the cassettes 102a to 102c is transmitted to the control apparatus 104 via the imaging unit connectors 107a to 107c, the platform connectors 206a to 206c, and the relay 103.

To carry out the long length imaging, first, the cassettes 102 are mounted and fixed onto the respective fixation positions of the platform 101 for the long length imaging. When the platform connectors 206 and the imaging unit connectors 107 are fitted to each other, respective main control circuits 150 inside the cassettes 102 are connected to the relay 103 via the imaging unit connectors 107, the platform connectors 206, and the network cables 205. As a result, a network including the cassettes 102 and the control apparatus 104 is formed. The cassettes 102 and the relay 103 are connected in an individually attachable and detachable manner by the fitting between the imaging unit connectors 107 and the platform connectors 206.

When the network is formed, each of the cassettes 102 communicates with the control apparatus 104, and control communication with each of the cassettes 102 is performed by software of the control apparatus 104. The control communication enables the software of the control apparatus 104 to recognize that each of the cassettes 102 is mounted on the platform 101, and also recognize a position where each of the cassettes 102 is mounted on a holder.

When the user completes an operation of mounting the cassettes 102, and the software is able to confirm normal mounting, completion of preparation is displayed on the touch panel monitor 108 connected to the control apparatus 104. The user checks a message indicating the completion of preparation and carries out imaging. As illustrated in FIG. 1, the imaging is carried out such that a subject is positioned in front of the platform 101 and the subject in a wide range extending across the plurality of cassettes 102 is captured by performing irradiation with the radiation a single time.

Figure 3:
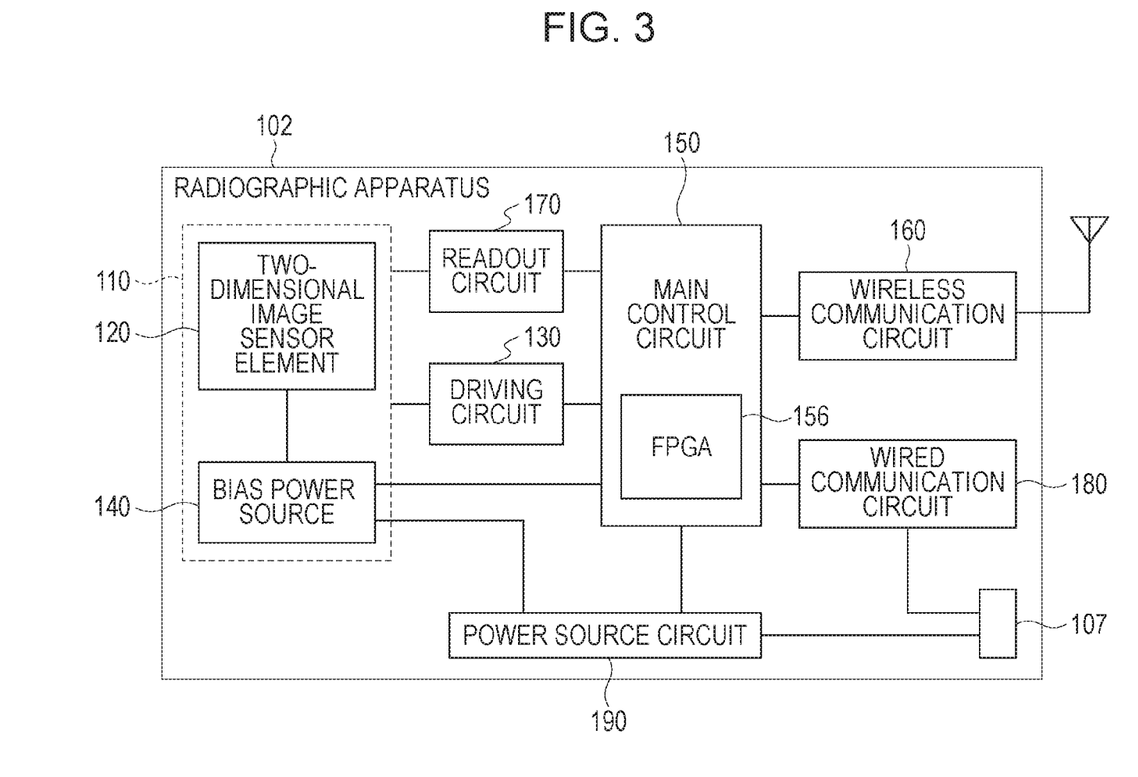
FIG. 3 is a block diagram illustrating a configuration of a cassette.

After the imaging, the main control circuit 150 of each of the cassettes 102 generates image data by performing scanning of a two-dimensional image sensor element 120. The generated image data is transferred to the control apparatus 104. In this case, the image data can be transferred using a communication path via a wired communication circuit 180 and the imaging unit connector 107 that are incorporated in the cassette 102, the platform connector 206, and the like. Alternatively, the image data can be transferred via a wireless communication circuit 160 incorporated in the cassette 102, and a wireless access point (not illustrated) connected to the control apparatus 104.

The control apparatus 104 performs image processing for rearranging the images received from the cassettes 102 by referring to recognized information about the positions where the cassettes 102 are mounted and connectively combining the images. The combined image is provided to the user as a long length imaging image that includes information of the subject in the wide range.

A configuration of each of the cassettes 102 according to the present embodiment will be described with reference to FIG. 3. The two-dimensional image sensor element 120 includes a pixel array in which a plurality of pixels are arrayed in a matrix, and generates an image based on distribution of intensity of the incident radiation. A driving circuit 130 supplies a driving signal to a row selection line that is commonly connected to pixels lined up in a row direction, and a readout circuit 170 extracts an image signal from a column signal line that is commonly connected to pixels lined up in a column direction. Each of the pixels includes a photoelectric conversion element with one end connected to a bias power source 140 and a switching element connected to the other end of the photoelectric conversion element. A base electrode of the switching element is connected to the row selection line, and the photoelectric conversion element and the column signal line are connected to a collector and an emitter.

The driving circuit 130 controls an ON state and an OFF state of the switching element by outputting the driving signal. When the switching element is brought into the OFF state, electric charge is accumulated as the image signal in a capacity of the photoelectric conversion element. When the switching element is brought into the ON state, the image signal is output via the column signal line. The image signal output from a radiation sensor 110 is read out as a digital signal by the readout circuit 170 constituted by an amplifier and an A/D converter for performing conversion into the digital signal.

The driving circuit 130 performs control of collectively applying off-state voltages and control of sequentially applying on-state voltages to the row selection lines. The off-state voltages make the radiation sensor 110 shift to an accumulation state. The control of sequentially applying the on-state voltages causes signals of the pixel array to be sequentially output to the readout circuit 170. As a result, an operation of initializing the pixel array before shifting to the accumulation state and an operation of reading out the image signal acquired from the accumulation are performed.

The main control circuit 150 integrally controls the cassette 102. The main control circuit 150 includes a processing circuit implemented by an FPGA (Field-Programmable Gate Array) 156, and thereby generates a radiographic image and performs image processing. The FPGA 156 performs processing for acquiring an image including a small data amount, for example, by binning processing for summing up values of adjacent 2×2 pixels, thinning-out processing for partially thinning out pixels and extracting a part of the pixels, processing for extracting a continuous region, or the like when acquiring a digital radiographic image.

Examples of the image processing performed by the FPGA 156 include dark correction for reducing a dark current component in a radiographic image, gain correction for correcting a variation in input/output characteristics of a pixel, correction of a defective pixel, and processing for reducing a noise such as a line noise.

The wireless communication circuit 160 and the wired communication circuit 180 transmit and receive a control command and data of signals from the control apparatus 104 and the radiation generation apparatus 100. The wireless communication circuit 160 transmits a signal indicating a state of the cassette 102 and the radiographic image. The wireless communication circuit 160 includes an antenna and performs wireless communication mainly when a wired cable is not connected to the imaging unit connector 107. The imaging unit connector 107 is connected to the wired communication circuit 180 so that wired communication is controlled. The imaging unit connector 107 is provided for communication and power supply, and communication information is transmitted to the wired communication circuit 180 and power is transmitted to a power source circuit 190. The power source circuit 190 includes a battery, and produces a voltage required for the operation of the cassette 102 to supply the voltage to each of the units.

The main control circuit 150 specifies whether wireless communication or wired communication is to be used. For example, the wired communication is specified when the wired cable is connected to the imaging unit connector 107, and the wireless communication is specified when the wired cable is not connected, but connection through the wireless communication is established. Neither communication method is specified when the wired cable is not connected and connection through the wireless connection is also not established. In this case, the radiographic image is not transmitted and is stored in a nonvolatile memory connected to the main control circuit 150.

When the radiographic image is transmitted with the communication method specified, the main control circuit 150 transfers a preview image including a smaller data amount than that of the radiographic image acquired by the radiation sensor 110 prior to the radiographic image. Then, the main control circuit 150 transmits a main image including data that is not included in the preview image after transmission of the preview image is completed.

By seeing the preview image, the control apparatus 104 side is able to quickly check whether the imaging has been appropriate. The preview image and the image including the data that is not included in the preview image can be transmitted based on the readout of the image signal by the readout circuit 170 and the generation of the preview image by the main control circuit 150. Alternatively, the transmission can be performed based on a signal from the control apparatus 104. In this manner, when the control apparatus 104 controls the communication with the plurality of cassettes 102, it is possible to reduce influence due to simultaneous transmission of large-volume data from the plurality of cassettes 102 and realize efficient image communication.

As one state of the cassette 102, there is a first state (so-called sleep state) in which power is supplied to the wireless communication circuit 160 and the wired communication circuit 180 and power is not supplied from the bias power source 140 to the two-dimensional image sensor element 120. There is a second state in which power is supplied from the bias power source 140 to the two-dimensional image sensor element 120. In the second state, an initialization operation (reset operation) is intermittently executed and the reset operation of the cassette 102 is repeatedly executed. There is a third state in which electric charge based on the radiation incident on the two-dimensional image sensor element 120 is accumulated. In the third state, generation of an image is performed by shifting to the accumulation state in response to an external instruction. The cassette 102 transmits a signal indicating the aforementioned state based on an external request signal.

In a case where the interface unit 203 is provided in the radiation generation apparatus 100, synchronized communication is performed between the radiation generation apparatus 100 and the cassettes 102. In response to pressing of the irradiation switch, the interface unit 203 transmits a first signal to each of the cassettes 102a to 102c. In accordance with the first signal, the driving circuit 130 of each of the cassettes 102a to 102c causes the two-dimensional image sensor element 120 to perform the initialization operation, and causes the two-dimensional image sensor element 120 to shift to the accumulation state. Based on completion of the initialization or the shift to the accumulation state, each of the cassettes 102a to 102c transmits a second signal to the interface unit 203. The interface unit 203 determines whether second signals are received from all the cassettes 102 to be used for the long length imaging, and when determining that the second signals are received, inputs a signal for permitting irradiation to the generation control unit 100b. Based on the signal for permitting irradiation, the radiation is emitted from the radiation source 100a. Such control enables prevention of emission of the radiation before each of the cassettes 102 is shifted to the accumulation state and reduces unnecessary exposure.

A case where the cassettes 102a and 102b of the plurality of cassettes 102a, 102b, and 102c have different sizes will now be described. When each of the cassettes 102 is shifted to the accumulation state, the driving circuit 130 completes the initialization operation by performing scanning up to the last row of the pixel array and is shifted to the accumulation state. At this time, because of the difference of the sizes, the cassettes 102a and 102b are different in timing when the initialization operation is completed. That is, the cassettes 102a and 102b are different in timing when the subsequent accumulation state ends. When the cassettes 102a and 102b are different in timing when being shifted to the accumulation state because of a difference of driving speeds, similarly, the cassettes 102a and 102b have different timing when the accumulation state ends.

Though control can be performed so that the radiation is emitted only during a period in which all the accumulation states of the plurality of cassettes 102 are overlapped, control for the accumulation states is preferably performed based on an irradiation period in order to perform imaging with an amount of irradiation much suitable for diagnosis. Examples of the control for the accumulation states based on the irradiation period include adjustment of periods of the initialization operation and the accumulation states based on information of the plurality of cassettes 102, control of the end of the accumulation of the plurality of cassettes 102 by an irradiation stop signal, and automatic detection of the end of emission of the radiation by the plurality of cassettes 102. As the period of the accumulation state is decided in advance in imaging using one cassette, control for the accumulation state based on the irradiation period is performed when switched to the long length imaging.

Figure 4:
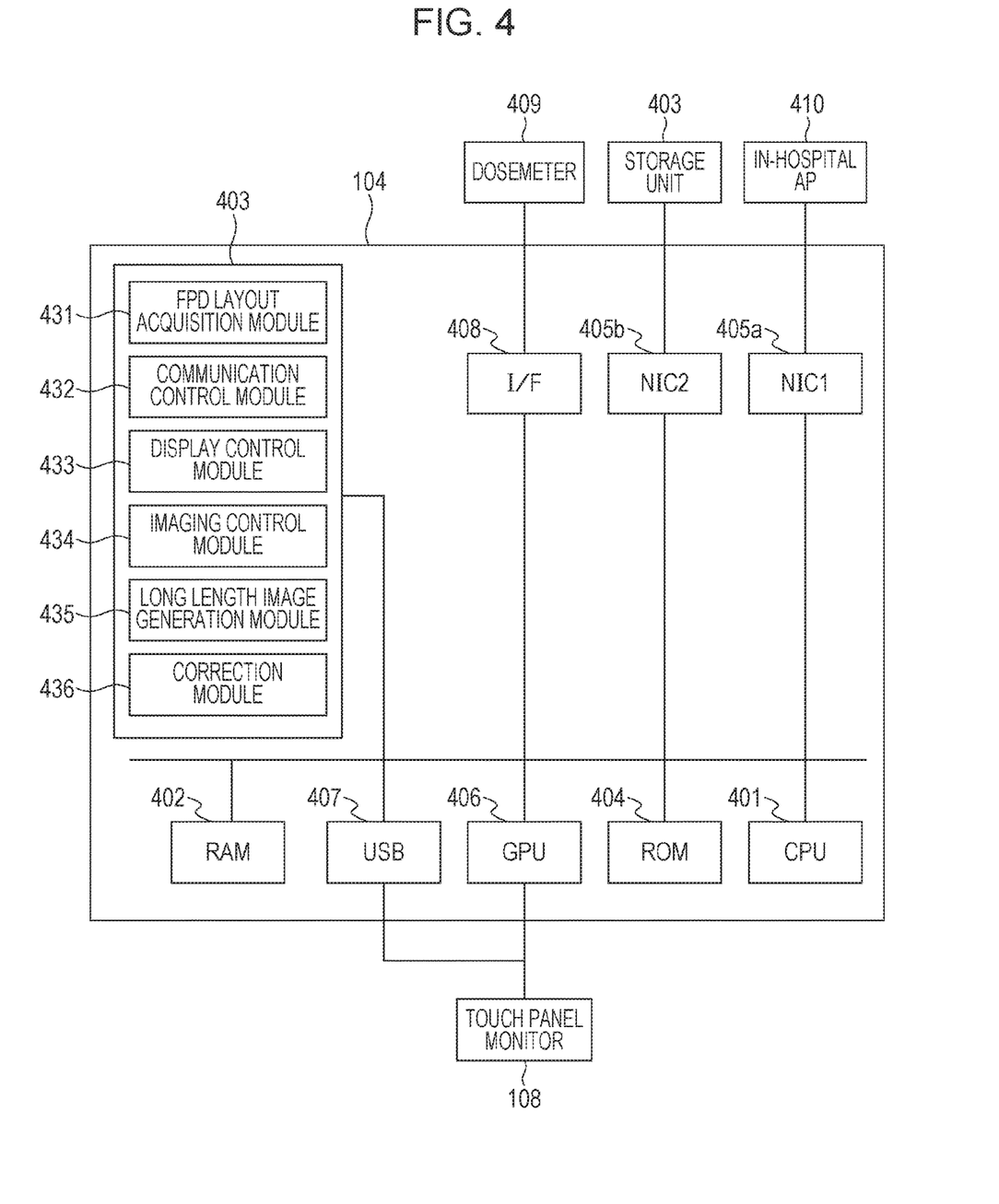
FIG. 4 is a block diagram illustrating a configuration of a control apparatus.

A configuration of the control apparatus 104 according to the present embodiment will be described with reference to FIG. 4. A CPU (Central Processing Unit) 401 is a control circuit that comprehensively controls the control apparatus 104 and each unit connected thereto. The control apparatus 104 can include a plurality of CPUs. A RAM (Random Access Memory) 402 is a memory used for developing a program (modules 431 to 436) and various parameters that are stored in a storage unit 403. The CPU 401 sequentially executes commands included in the program developed in the RAM 402. The storage unit 403 is a memory such as an HDD (Hard Disk Drive) or an SSD (Solid State Drive), and stores the program, a radiographic image, such as a long length image acquired by imaging, imaging order, imaging information, and other various parameters.

NICs (Network Interface Cards) 405 are communication units that communicate with an external apparatus. A first NIC 405a is connected to an in-hospital AP (Access Point) 410 for connecting to an in-hospital network and a second NIC 405b is connected to the relay 103 that relays the communication of the radiographic system. A GPU (Graphic Processing Unit) 406 is an image processing unit and performs image processing based on control from the CPU 401. An image acquired as a result of the image processing is displayed on the touch panel monitor 108. A USB (Universal Serial Bus) 407 is a communication unit that acquires information of an operation input from the touch panel monitor 108 which is interpreted as the operation input by the CPU 401. A communication I/F (Interface) 408 is a communication unit such as an RS 232, Ethernet, or a USB, and communicates with a Dosemeter (dose measurement device) 409 to receive dose information.

An FPD (Flat-Panel Detector) layout acquisition module 431 acquires apparatus information of the cassettes 102 to be used for performing one long length imaging and information indicating a layout relationship. The apparatus information is information related to a pixel size of the pixel array, a total number of pixels, an imaging size, and a preparatory period serving as a period during which one frame of the pixel array is subjected to scanning (including readout and initialization). The apparatus information can also include a period of a difference between preparatory periods of the cassettes 102. Such apparatus information is saved in a table format for each of the cassettes 102 and for each type (model) of the cassettes 102.

The information indicating the layout relationship is information indicating how the cassettes 102a to 102c are laid out and can include information indicating rotation states of the cassettes 102a to 102c. The information indicating the layout relationship is acquired by the CPU 401 based on information that is received by the second NIC 405b, and indicates communication paths of the cassettes 102 and correspondence information that is stored in the storage unit 403 and indicates correspondence relationships between the communication paths and the layout of the cassettes 102. For example, in a case where the platform connectors 206 are fixed to the housing units 201, as illustrated in FIG. 2, the layout of the plurality of cassettes 102 is identified by referring to the information about the communication paths. As the information about the communication paths, in a case where the relay 103 is a layer 2 network switch, the relay 103 uses an operation of learning relationships between physical ports and MAC addresses and acquires correspondence relationships between the cassettes 102 and the physical ports.

The information indicating the layout relationship acquired in this manner is stored in the storage unit 403. Alternatively, the second NIC 405b can receive the information itself indicating the layout relationship. In this case, the relay 103 or the platform 101 has a function of acquiring the information indicating the layout relationship based on the information about the communication paths, and the like.

The information indicating the layout relationship is referred to in a process of execution of a long length image generation module 435, and used in processing for stitching a plurality of radiographic images. In this case, the information indicating the layout relationship is used for identifying which radiographic images have an overlap region. The information indicating the layout relationship is referred to by the CPU 401 to decide which radiographic image is to be subjected to execution of correction processing for removing a structure appearing therein in a process of execution of a correction module 436. The information indicating the layout relationship in this case is information for identifying in which image of the cassettes 102 the structure appears, and serves as information for identifying which of the cassettes 102 is located in the middle in an imaging system illustrated in FIG. 1.

A communication control module 432 controls communication by the first NIC 405a and the second NIC 405b. When the communication control module 432 is executed, signals for causing the cassettes 102 to shift to the second state are transmitted to the cassettes 102 based on an operation input from the touch panel monitor 108. By an operation for selecting one of a plurality of imaging conditions included in the imaging order, the imaging condition is identified by the CPU 401 so that the operation input is performed. Based on the operation input, the second NIC 405b transmits, to the cassettes 102, the signals for shifting the states. The second NIC 405b receives response signals thereto.

When the communication control module 432 is executed, the control apparatus 104 receives the radiographic image from each of the cassettes 102. At this time, the control apparatus 104 first receives a preview image (first image) including a small data amount and then receives a main image (second image) from each of the cassettes 102. In this case, when the preview image is received from one cassette 102, receipt of the image from the other cassettes 102 is restricted. Therefore, each of the cassettes 102 starts transmission of the image in response to an instruction from the control apparatus 104, and one cassette 102 starts transmission of the main image based on completion of the reception of the preview images from all the cassettes 102. Thus, a large volume of data is prevented from being transmitted to the relay 103 simultaneously from the plurality of cassettes 102 so that efficiency of communication is improved.

As described above, there is a transmission method (second transmission method) in which each of the cassettes 102 transmits an image in response to an instruction signal and a transmission method (first transmission method) in which a radiographic image is transmitted in response to readout of an image signal. The transmission method to be executed is specified based on a signal from the control apparatus 104. The first transmission method is specified when the cassettes 102 perform the wireless communication and the second transmission method is specified when the cassettes 102 perform the wired communication. When the transmission method is specified based on a communication form in this manner, the cassettes 102 specify the transmission method regardless of an external signal.

A display control module 433 controls a content of a display screen displayed on the touch panel monitor 108. Examples thereof include processing for displaying the imaging condition for the long length imaging and processing for displaying the generated long length image. The CPU 401 determines whether any one of the plurality of cassettes 102 is in the first state or all the cassettes 102 are in the second state based on the information indicating the states of the cassettes 102. When the display control module 433 is executed, information indicating a result of the determination is displayed on the display screen. By displaying an indication whether all the cassettes 102 are in the state capable of imaging, instead of displaying individual indications of the state of each of the cassettes 102, the user can intuitively recognize whether the long length imaging can be performed. By displaying an indication whether all the cassettes 102 are in the state capable of imaging and displaying individual indications of the state of each of the cassettes 102 it can also be recognized which cassette 102 is not able to perform imaging.

An imaging control module 434 causes the CPU 401 to integrally control execution of radiographic imaging including the long length imaging. Specification of the imaging condition based on an operation input, transmission of a signal for requesting the state of each of the units of the cassette 102, and reception of a radiographic image are controlled via the imaging control module 434.

A long length image generation module 435 generates a long length image from a plurality of radiographic images using the CPU 401 and the GPU 406. The long length image is generated by positioning processing for defining a positional relationship from among the plurality of radiographic images. The positioning processing includes rough adjustment processing for deciding a rough layout from among the images and fine adjustment processing for adjusting positions from among the images with precision of several pixels or precision of one pixel or less.

A correction module 436 uses the CPU 401 and the GPU 406 to perform processing for correcting an influence due to characteristics of a sensor and correction processing for reducing a structure appearing in a radiographic image.

In another embodiment, the control apparatus 104 can include the function of the relay 103. In this case, it is configured in such a manner that three second NICs 405b that communicate with the cassettes 102 are provided and cables connected to the cassettes 102 are directly connected to the control apparatus 104.

Figure 6:
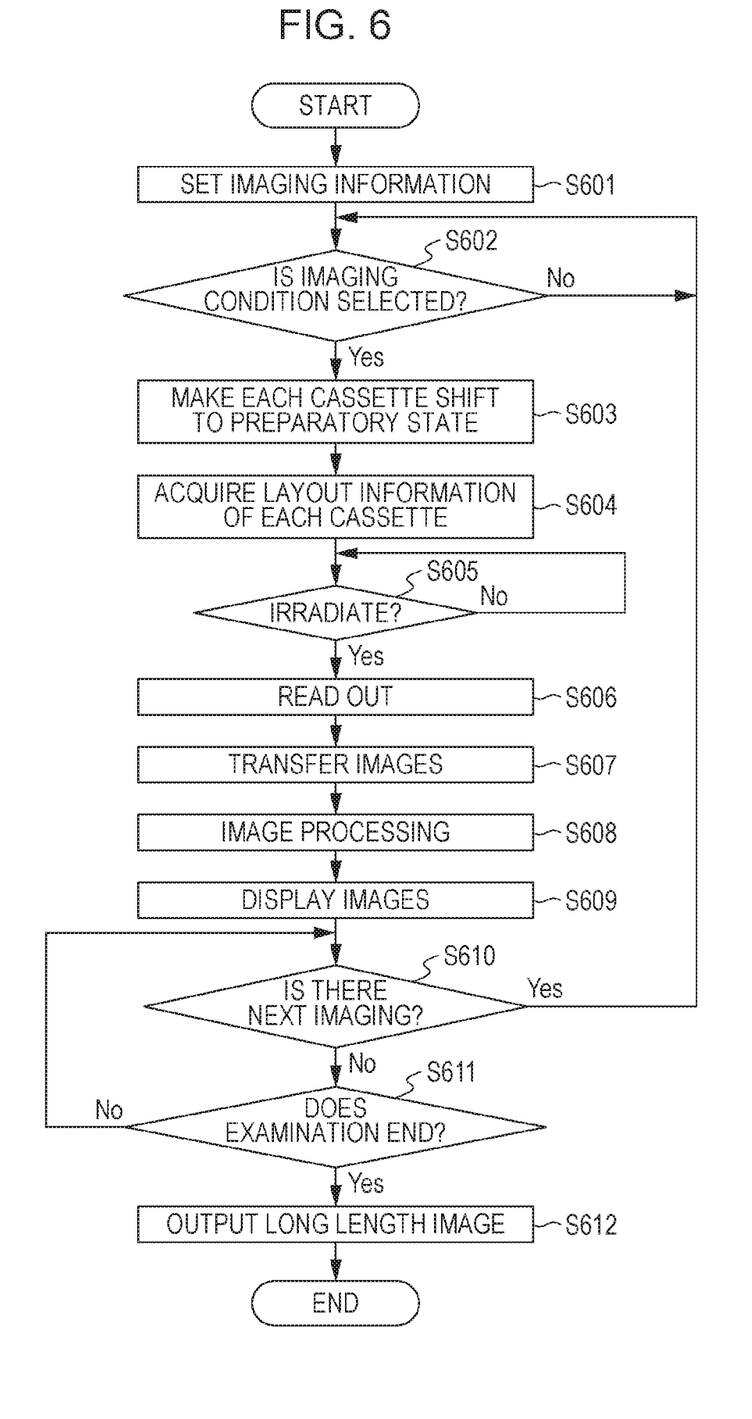
FIG. 6 is a flowchart illustrating a flow of processing associated with long length imaging.

A flow of processing related to the long length imaging will be described with reference to a flowchart of FIG. 6. A processing entity is the CPU 401 of the control apparatus 104 unless otherwise noted. Steps S601 to S612 are executed by the imaging control module 434.

Figure 5:
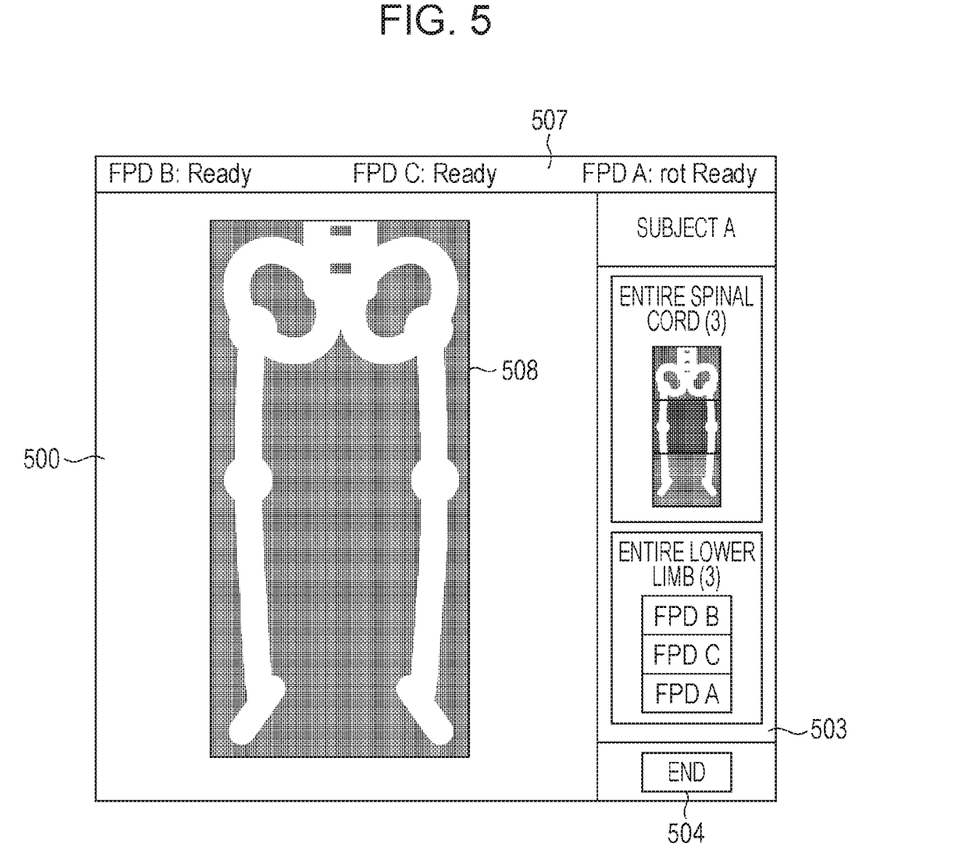
FIG. 5 is a schematic view illustrating an example of a display screen.

At step S601, a piece of imaging information (examination information) from the RIS 151 is set as an examination target. The setting is performed when the display control module 433 is executed and the user selects one of the plurality of pieces of examination information displayed in a list format on a display screen 500.

At step S602, whether an operation input for selecting an imaging condition for the long length imaging that is included in the imaging information is performed is determined. When the imaging information includes a plurality of imaging conditions, information corresponding to the plurality of imaging conditions is displayed in an imaging information area on the display screen 500, and whether an operation input for selecting one of the imaging conditions is performed by the user is determined. The determination processing of step S602 is repeated until the operation input for the selection is performed. When the operation input for the selection is performed, the procedure proceeds to next processing. The procedure can automatically proceed to step S603 regardless of the processing of step S602 when the imaging information is only information about the imaging condition corresponding to the imaging.

At step S603, the imaging condition for the long length imaging selected by the operation input is specified. Based on the imaging condition that is specified, the CPU 401 causes the second NIC 405b to transmit signals to cause the plurality of cassettes 102 involved in the long length imaging to shift to the preparatory state. In response to the signals, a bias voltage is applied to the two-dimensional image sensor element 120 by controlling the bias power source 140 by the main control circuit 150 in each of the cassettes 102. Then, initialization of reading out image signals from the pixel array is performed by the driving circuit 130 to read out dark current signals accumulated in pixels. After completion of the initialization, each of the cassettes 102 transmits state information indicating that each of the cassettes 102 is in the second state to the control apparatus 104.

At step S604, the apparatus information of the plurality of cassettes 102 to be used for the long length imaging and the layout information indicating the layout relationship are acquired via the communication paths. Information related to driving, such as a readout period, of the apparatus information can be actually measured and recorded by actually operating the cassettes 102. For the layout relationship, information of the communication paths of the cassettes 102 is acquired from the relay 103. The relay 103 is provided with a plurality of physical ports to which cables from the platform connectors 206a to 206c respectively provided in the housing units 201a to 201c are connected. The relay 103 identifies from which physical port each of the signals from the cassettes 102 is input, thereby generating information indicating the correspondence relationships between the physical ports and the cassettes 102, that is, the communication paths of the cassettes 102.

The CPU 401 receives such information from the second NIC 405b. The CPU 401 acquires the apparatus information and the information indicating the layout relationship from the information indicating the communication paths acquired in this manner. The information indicating the layout relationship is displayed as the information indicating the layout relationship among the cassettes (FPD A to FPD C) to be used for the long length imaging in imaging information 503 on the display screen 500 of FIG. 5. Based on the imaging condition for the long length imaging and the apparatus information, the control apparatus 104 transmits, to the radiation generation apparatus 100 and the cassettes 102, information for controlling the accumulation states based on an irradiation period described below.

At step S605, whether the irradiation switch is pressed is determined. When the irradiation switch is pressed, the procedure proceeds to step S606. Whether the irradiation switch is pressed is notified based on the state information of the cassettes 102 displayed on the display screen 500 as described above.

At step S606, the driving circuit 130 of each of the cassettes 102 reads out an image signal, acquired by detecting the radiation that is emitted, by the readout circuit 170 and generates a digital radiographic image.

At step S607, the wireless communication circuit 160 or the wired communication circuit 180 of the cassette 102 transmits the generated digital radiographic image to the control apparatus 104. The cassette 102 transmits a preview image and then transmits a main image, thereby completing the transmission of the radiographic image acquired through the imaging. When the radiographic image is transmitted via the wireless communication circuit 160, each of the cassettes 102 sequentially transmits the preview image and the main image in response to the readout of the image signal. The transmission is performed asynchronously with the other cassettes. When the image is transmitted via the wired communication circuit 180, in consideration of a problem of shortage of a communication capacity, the main image is not transmitted until the transmission of preview images from all the cassettes 102 is completed.

At step S608, the radiographic images output from the cassettes 102 are subjected to image processing using the GPU 406. Specific examples include processing for generating a long length image using the long length image generation module 435 and processing for reducing a structure image with using the correction module 436. First, processing for acquiring a preview long length image from the plurality of preview images is performed, and then processing for acquiring a long length image from the plurality of main images is performed. The processing for acquiring the long length image is performed using the layout information acquired at step S604.

At step S609, the preview long length image and the main long length image that are subjected to the image processing are displayed on a display unit.

At step S610, whether there is an imaging condition on which the imaging has not been performed is determined. When there is such an imaging condition, the procedure proceeds to step S602 and long length imaging based on a new imaging condition is performed. When there is no imaging condition on which the imaging has not been performed, whether to end examination is determined at step S611. When the examination does not end, processing for waiting for addition of an imaging condition on which the imaging has not been performed or an instruction to end the examination is performed (steps S610 and S611). When an examination end button 504 is pressed at this time, the examination ends.

At step S612, the first NIC 405a outputs a DICOM image file of the long length image to the PACS 153. Thus, the examination that includes the long length imaging ends.

As described above, in the long length imaging, when an exposure period of X-rays does not fall within accumulation periods in imaging operations of all the cassettes, an artifact can be generated in a captured image.

In particular, when cassettes that are different in a preparatory period from a preparatory operation to start of accumulation in an imaging operation are used, in a cassette whose preparatory period is shorter than the exposure period of X-rays, the exposure of X-rays is not completed when the accumulation ends and the exposure of X-rays is continued even after the end of the accumulation. Thereby, an artifact is generated in an image captured by the cassette whose preparatory period is short. Thus, in the present embodiment, in a case where cassettes that are different in a preparatory period from an exposure request of X-rays to start of accumulation are used in combination, timing when the accumulation starts in each of the cassettes is controlled so that the exposure period of X-rays is included in the accumulation periods of all the cassettes. Such control enables prevention of artifact generation due to continuation of radiation exposure even after the accumulation ends.

Example 1

A method for controlling timing to start accumulation in each apparatus in the present example will be described.

Figure 7:
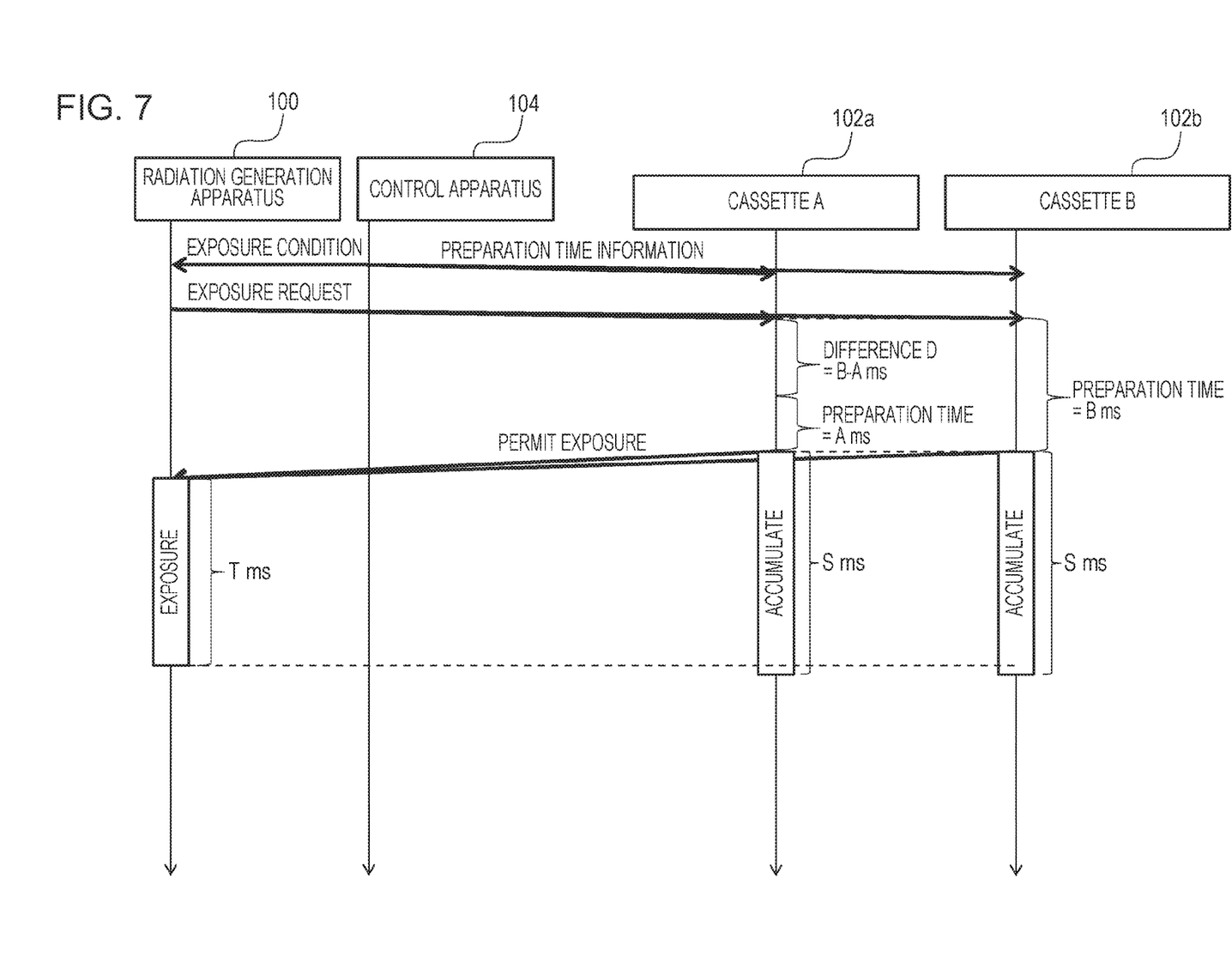
FIG. 7 is a time chart illustrating a flow of an operation according to Example 1.

FIG. 7 is a time chart for controlling, when two cassettes whose preparatory periods are different from each other are used, timing to start accumulation of image signals of the cassettes.

The control apparatus 104 stores information of preparatory periods and accumulation periods of the cassetteA 102a and the cassetteB 102b. In another embodiment, the information can be held by the radiation generation apparatus 100. It is assumed that a preparatory period A of the cassetteA 102a is 200 msec and a preparatory period B of the cassetteB 102b is 500 msec, a difference D between the preparatory periods of the cassettes is 300 msec, and an accumulation period S is 1 sec in common. An X-ray exposure period T is 800 msec.

First, before imaging, the control apparatus 104 notifies each of the cassettes 102 of imaging information, such as the X-ray exposure period T, the accumulation period S, and the maximum preparatory period B based on the imaging order. The control apparatus 104 notifies the radiation generation apparatus 100 of an exposure condition, such as the X-ray exposure period. The timing when the imaging information is notified is not limited to timing before the imaging and the notification can be performed at the same timing with an exposure request.

When a request of X-ray exposure is made from the radiation generation apparatus 100, the cassetteA 102a calculates the difference D by subtracting the preparatory period A from the preparatory period B. The preparatory period to be extended is not limited to the difference D and can be set to any period as long as the X-ray exposure period is included in the accumulation periods of all the cassettes. Then, preparatory period information is notified, together with an exposure request signal, to the cassette used for the imaging. The cassetteA 102a extends the period by the difference D and sets the resultant as a current preparatory period for the imaging. Thus, each of the cassettes transmits an exposure permission signal to the radiation generation apparatus 100 and starts the accumulation operation after substantially the same preparatory period B has lapsed.

Upon receipt of the exposure permission signal, the radiation generation apparatus 100 starts exposure of X-rays for the period T. The radiation generation apparatus 100 ends the exposure of X-rays after the period T has lapsed, and the cassetteA 102a and the cassetteB 102b end the accumulation and transmit image data to the control apparatus 104.

The difference D can be calculated by the control apparatus 104 and transmitted as the preparatory period information to the cassetteA 102a. The start of the preparatory period A of the cassetteA 102a can be controlled by the radiation generation apparatus 100 or the control apparatus 104. The radiation generation apparatus 100 can transmit the exposure request to the cassetteA 102a after the difference D has lapsed or the control apparatus 104 receives the exposure request and transmits the exposure request to the cassetteA 102a after the difference D has lapsed.

Example 2

Figure 8:
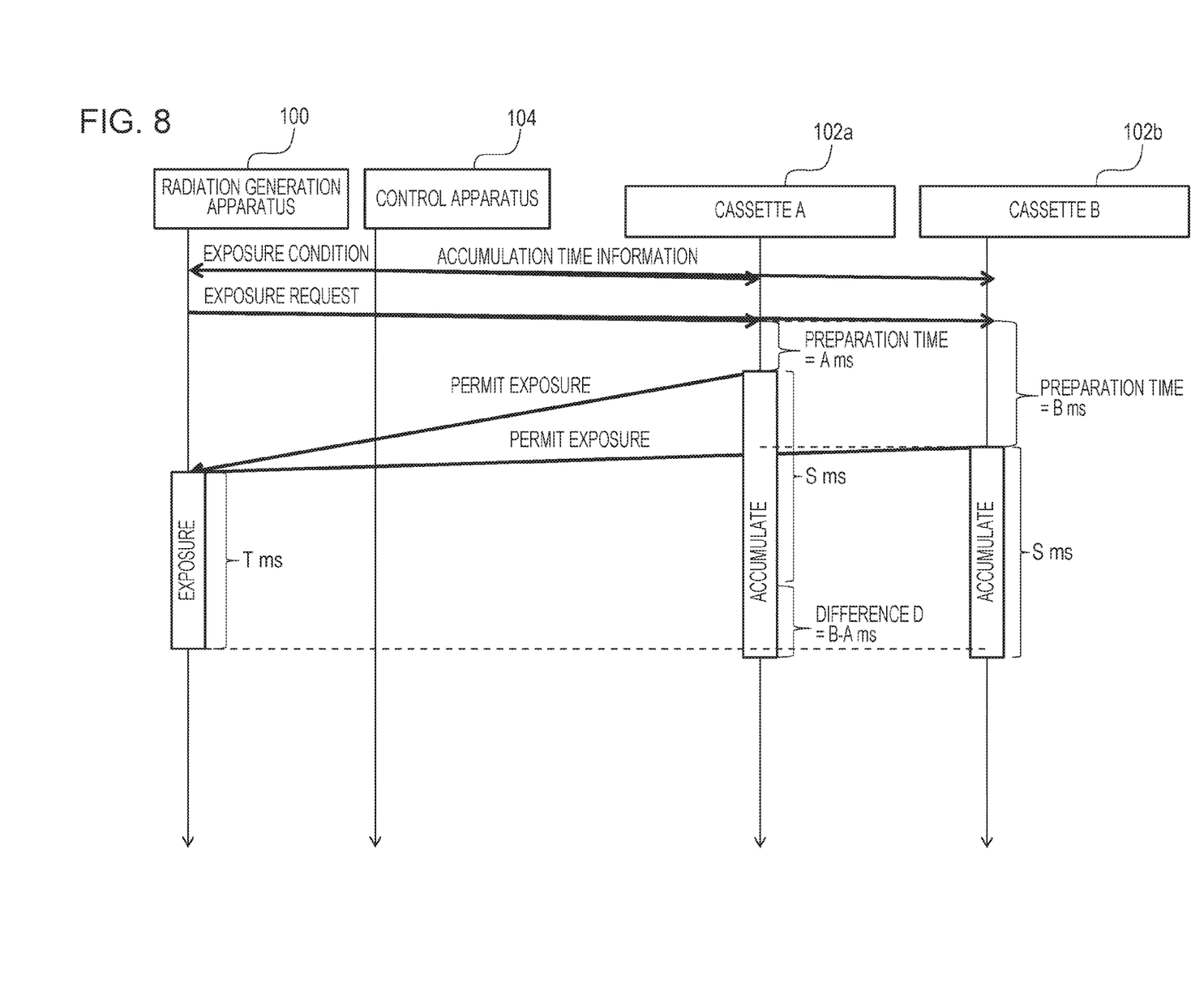
FIG. 8 is a time chart illustrating a flow of an operation according to Example 2.

FIG. 8 is a time chart for extending an accumulation period of one of the cassetteA 102a and the cassetteB 102b when imaging is performed using the cassetteA 102a and the cassetteB 102b. The present example is similar to Example 1 except that the accumulation period of the cassetteA 102a, whose preparatory period is short, is extended.

First, before imaging, the control apparatus 104 notifies each of the cassettes of imaging information, such as the X-ray exposure period T and the accumulation period S, based on the imaging order.

The control apparatus 104 calculates the difference D (=B−A) to be extended from the preparatory period information (the preparatory period A and the preparatory period B longer than A) of each of the cassettes, which is stored, and selects a cassette (the cassetteA 102a in the present example) to which the difference D is to be notified. The accumulation period to be extended is not limited to the difference D and can be set to any period as long as the X-ray exposure period is included in the accumulation periods of all the cassettes. Then, accumulation period information is provided, together with an exposure request signal, to the cassette used for the imaging. The cassetteA 102a receives the difference D (=B−A), adds the difference D to a predetermined accumulation period, and sets the resultant as a new accumulation period. The cassetteB 102b receives the difference D (=0) and does not change the accumulation period.

The accumulation period of the cassetteA 102a can be controlled such that the control apparatus 104 transmits, as an updated accumulation period S', to the cassetteA 102a, a period obtained by calculating the difference D and adding the difference D to an initial (unchanged) accumulation period S.

Example 3

Figure 9:
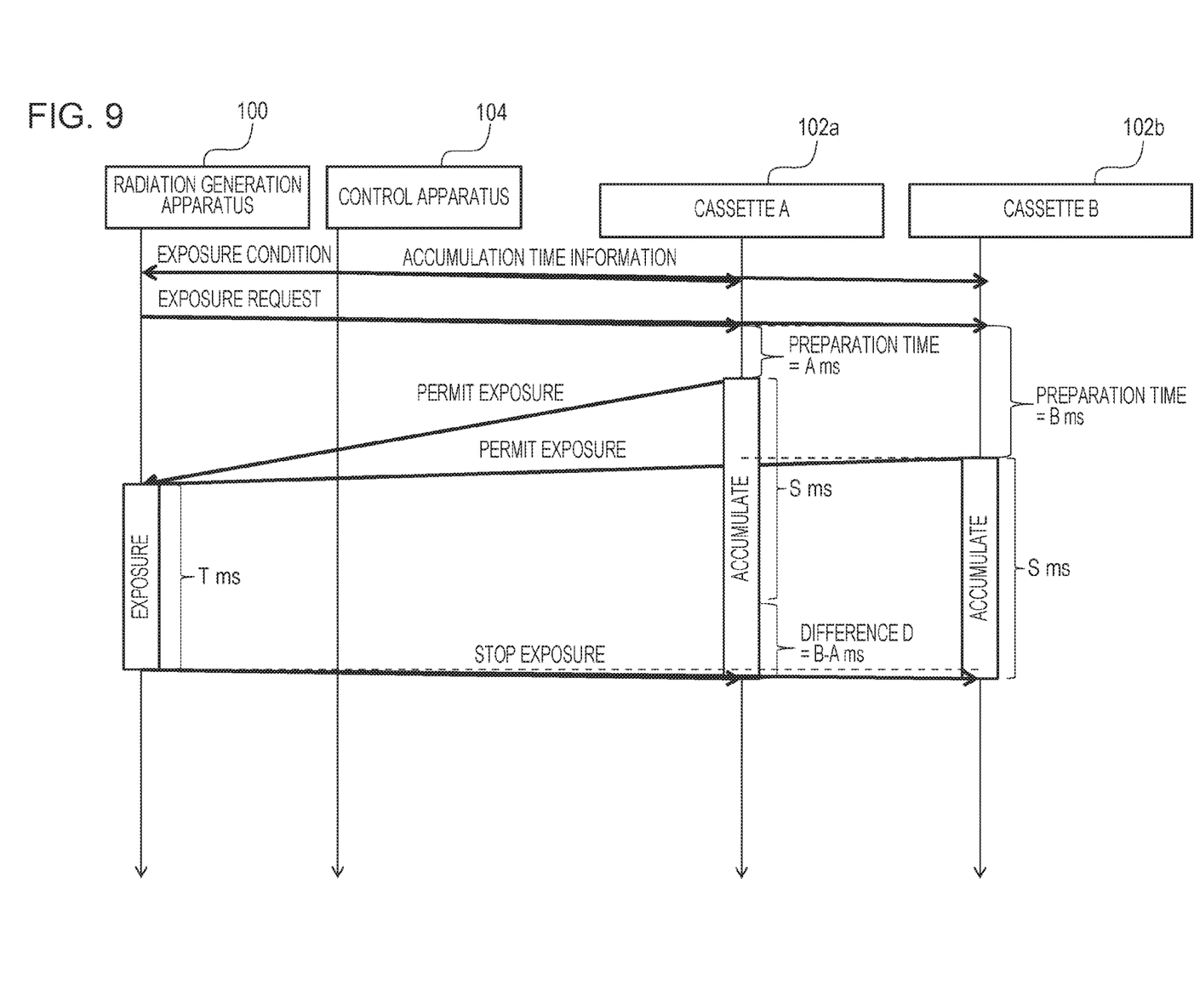
FIG. 9 is a time chart illustrating a flow of an operation according to Example 3.

FIG. 9 is a time chart for extending an accumulation period of at least one of the cassetteA 102a and the cassetteB 102b until an exposure stop signal is received, when imaging is performed using the cassetteA 102a and the cassetteB 102b. The present example is similar to previous examples, except that the accumulation period of the cassetteA 102a, whose preparatory period is short, ends by the exposure stop signal.

First, before imaging, the control apparatus 104 notifies each of the cassettes 102 of accumulation period information such as the X-ray exposure period T and an accumulation end condition based on the imaging order. In the long length imaging, such notification leads to switching control of at least a cassette whose preparatory operation is short to control to end accumulation by the exposure stop signal, while the accumulation end is managed in a predetermined period in normal imaging using one cassette. In the present example, control of all the cassettes 102 is switched. The control apparatus 104 notifies the radiation generation apparatus 100 of setting of transmission of the exposure stop signal. Timing when the imaging information is notified is not limited to timing before the imaging, and the notification can be performed at the same timing with the exposure request.

Each of the cassettes 102 continues the accumulation until the exposure stop signal is received from the radiation generation apparatus 100. The radiation generation apparatus 100 ends the exposure after the X-ray exposure period T has lapsed, and notifies all the cassettes 102 of the exposure stop signal. Upon receipt of the exposure stop signal, each of the cassettes 102 ends the accumulation.

In any example, dark correction for reducing a dark current component of a radiographic image needs to be performed. An image for the dark correction can be created based on a dark current component before imaging of a long length image or created based on a dark current component acquired in the same period as the accumulation period immediately after imaging of the radiographic image. When the accumulation period of the radiographic image and the accumulation period of the dark current component are different, correction can be performed so that data of the dark current component matches the accumulation period of the radiographic image.

An improved long length image is obtained even when imaging is performed by combining portable radiographic apparatuses whose preparatory periods from a request of X-ray exposure to start of accumulation are different.

While the present disclosure has been described with reference to exemplary embodiments, it is to be understood that the exemplary embodiments are not seen to be limiting. The scope of the following claims is to be accorded the broadest interpretation so as to encompass all such modifications and equivalent structures and functions.

This application claims the benefit of Japanese Patent Application No. 2016-237690 filed Dec. 7, 2016, which is hereby incorporated by reference herein in its entirety.

What is claimed is:

1. A control apparatus for a radiographic system in which long length imaging is performed using a plurality of radiographic apparatuses that each includes an accumulation period enabling accumulation of electric charge corresponding to incident radiation and a preparatory period including a period to perform initialization operation, at least one of the plurality of radiographic apparatuses including a different preparatory period, the control apparatus comprising:
a memory storing instructions; and
a control circuit that executes the instructions to:
control the plurality of radiographic apparatuses and a radiation generation apparatus so that an exposure period of the radiation generation apparatus is included in a period in which accumulation periods of all the plurality of radiographic apparatuses overlap.

2. The control apparatus according to claim 1, wherein the control circuit further executes the instructions to delay starting a preparatory period of a radiographic apparatus whose preparatory period is short from among the plurality of radiographic apparatuses based on a difference between preparatory periods of the plurality of radiographic apparatuses.

3. The control apparatus according to claim 1, wherein the control circuit further executes the instructions to extend an accumulation period of a radiographic apparatus whose preparatory period is short from among the plurality of radiographic apparatuses based on a difference between preparatory periods of the plurality of radiographic apparatuses.

4. The control apparatus according to claim 1, wherein the control circuit further executes the instructions to control the radiation generation apparatus to output a stop signal of radiation to each of the plurality of radiographic apparatuses to end the accumulation period.

5. The control apparatus according to claim 1, wherein the control circuit further executes the instructions to control the radiation generation apparatus to simultaneously radiate the radiation to the plurality of radiographic apparatuses.

6. The control apparatus according to claim 1, wherein the control circuit further executes the instructions to, based on pressing of an irradiation switch, start the exposure period by causing the radiation generation apparatus to start emission of radiation.

7. The control apparatus according to claim 1, wherein the control circuit further executes the instructions to control, during a readout period of the preparatory period, reading an image signal for one frame from a pixel array from each of the radiographic apparatuses in which pixels are arrayed in a matrix.

8. The control apparatus according to claim 7, wherein the control circuit further executes the instructions to acquire apparatus information including information about the readout period from each of the radiographic apparatuses and control the accumulation period based on the apparatus information.

9. The control apparatus according to claim 8, wherein the accumulation period is controlled based on an imaging condition input by a user operation.

10. The control apparatus according to claim 8, wherein the apparatus information includes one or more of a size of the pixel array, a total number of pixels, and an imaging size.

11. A radiographic system, comprising:
a control apparatus;
a radiation generation apparatus that generates radiation; and
a plurality of radiographic apparatuses that generate image signals by detecting the radiation and outputting the image signals to the control apparatus,
wherein the control apparatus includes:
a memory storing instructions, and
a control circuit that executes the instructions to:
control the radiographic apparatus and the radiation generation apparatus so that an exposure period of the radiation generation apparatus is included in a period in which accumulation period of all the plurality of radiographic apparatuses overlap.

12. The radiographic system according to claim 11, wherein all the accumulation periods of the plurality of radiographic apparatuses are equal before being changed.

13. A control method for a radiographic system in which long length imaging is performed using a plurality of radiographic apparatuses, the control method comprising the steps of:
acquiring information of a preparatory period to perform initialization operation from each of the plurality of radiographic apparatuses; and
based on at least one of the plurality of radiographic apparatuses including different information of a preparatory period, controlling the plurality of radiographic apparatuses and a radiation generation apparatus so that an exposure period of the radiation generation apparatus is included in a period in which accumulation periods of all the plurality of radiographic apparatuses overlap.

14. The control method according to claim 13, wherein control is performed to delay starting a preparatory period of a radiographic apparatus whose preparatory period is short from among the plurality of radiographic apparatuses based on a difference between preparatory periods of the plurality of radiographic apparatuses.

15. The control method according to claim 13, wherein control is performed to extend an accumulation period of a radiographic apparatus whose preparatory period is short from among the plurality of radiographic apparatuses based on a difference between preparatory periods of the plurality of radiographic apparatuses.

16. The control method according to claim 13, wherein control is performed so that the radiation generation apparatus outputs a stop signal of radiation to each of the plurality of radiographic apparatuses to end the accumulation period.

17. The control method according to claim 13, wherein accumulation periods of the plurality of radiographic apparatuses are changed from accumulation periods that are all equal.

18. The control method according to claim 13, wherein control is performed to, based on pressing of an irradiation switch, start the exposure period by causing the radiation generation apparatus to start emission of radiation.

19. The control method according to claim 13, wherein apparatus information including information about the readout period is acquired from each of the radiographic apparatuses and the accumulation period is controlled based on the apparatus information.

20. The control method according to claim 13, wherein the accumulation period is controlled based on an imaging condition input by a user operation.

* * * * *